United States Patent [19]

Barberet et al.

[11] Patent Number: Plant 5,419

[45] Date of Patent: Mar. 19, 1985

[54] CARNATION NAMED LONDRIOKA

[75] Inventors: Nicole Barberet; Yves Ducloux, both of Antibes, France

[73] Assignee: Laboratoire de Physiologie Vegetale de La Londe, Antibes, France

[21] Appl. No.: 517,369

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new and distinct carnation cultivar characterized by the substantially all white color of its medium sized blooms which are borne singly on strong, rather rigid stems of medium length and having moderately abundant foliage. This plant is also distinguished by its vigorous and upright growth habit and its profuse production of blossoms during each of its recurrent blooming seasons.

1 Drawing Figure

BACKGROUND OF THE NEW PLANT

Our new carnation plant is the result of breeding efforts carried on by us since 1977 with the object of developing new and distinctive varieties of carnations having attractive color and good quality of flower form and plant growth habits. Our new plant originated as a seedling at La Londe, Les Maures, France, by a cross of selected and individually identified plants growing among our collection of breeding stock maintained by us at La Londe and this particular plant was selected by us for propagation and test because of its unique almost pure white color and its apparently advantageous growth habit. The discovery plant was propagated by us at La Londe, France, by means of cuttings, and the newly propagated plants appeared to possess all of the distinctive characteristics of the parent plant. Continued propagation of this plant under our direction, by means of cuttings, through several successive generations, has demonstrated that the novel and distinctive characteristics of this new plant hold true from generation to generation and appear to be firmly fixed.

DESCRIPTION OF THE DRAWING

Our new carnation cultivar is illustrated by the accompanying photographic drawing which shows, in full color, a typical arrangement of buds, partially opened flowers and full blooms, the color rendition being as it is herein specified.

DESCRIPTION OF THE NEW PLANT

The following is a detailed description of our new carnation variety based upon characteristics of greenhouse grown plants observed at La Londe, France, in the Spring of 1983, the color designations being according to The R.H.S. Colour Chart of The Royal Horticultural Society at London, England.

THE PLANT

Origin: Seedling

Parentage:

*Seed parent.*—Stock Variety No. 8 B 1 (unpatented).

*Pollen parent.*—Stock Variety No. 70 B 1 (unpatented). These unnamed varieties are individually identified in our permanent records and are included in our collection of carnation plants maintained for breeding purposes at La Londe, Les Maures, France.

Classification:

*Botanic.*—Dianthus caryophyllus.

*Commercial.*—Standard carnation.

Form: A medium tall and erect bush.

Height: Averaging about 103 cm. at eight months.

Main stem: Less than 15 cm. long due to pinching.

Branching character: Rather few branches with at least four stems being emitted near the ground.

Growth habit: Vigorous and upright with rather rigid, strong stems.

Foliage:

*Quantity.*—Moderately abundant.

*Number of leaves.*—More than 120.

*Size of leaf.*—About 16 cm. long and 1.3 cm. wide, in average at the seventh node.

*Leaf shape.*—Spindle shaped with rolled margins.

*Texture.*—Leathery.

*Color.*—Upper side — 189A. Under side — 189A.

*Ribs and veins.*—Hardly noticeable.

*Rachis.*—Hardly noticeable.

THE BUD

Size: Medium. Diameter — Averages about 2.2 cm. Length — Averages about 3.3 cm.

Shape: Ovoid

Rate of opening: Normal for carnations.

Color of petals:

*When sepals first divide.*—Pure White.

*When petals begin to unfurl.*—Pure White.

Sepals:

*Shape.*—Joined at the lower part with upper part of ovate character and having a sharply pointed tip.

*Number.*—5 Or 6.

*Character.*—Sepals are hooded over the bud and curl back lightly when the flowers open.

*Color.*—Inside — Greenish White. Outside — 138A and 144D.

*Striae.*—Longitudinal

Calyx:

*Form.*—Bell shaped.

*Size.*—Medium.

*Splitting.*—Sometimes the calyx does split.

*Aspect.*—Smooth.

Flower stem:

*Length.*—About 74 cm.
*Character.*—Erect and rather rigid.
*Color.*—189A.

THE FLOWER

Blooming habit: Recurrent, blooming profusely in mid-season of Spring and Fall.
Size of Bloom: Medium. Diameter — About 8.2 cm. in average.
Borne: Singly.
Shape: When bloom first opens, high centered. When bloom matures, ball shaped.
Petalage:
*Number.*—Averaging about 61.
*Arrangement.*—Imbricated.
*Form.*—Fan shaped with rounded angle and finely serrated outer edge.
*Texture.*—Soft.
*Appearance.*—Satiny.
*Color.*—Outer petals: Body — Pure White and 155D. Base — Greenish White. Reverse side — Pure White and 155D. Inside petals: Upper side — Body: Pure White and 155D. Base: Greenish White. Reverse side — Pure White and 155D.
Flower stem:
*Length.*—About 74 cm., cut at tenth node.
*Character.*—Upright and of good strength.
*Color.*—189A.
Fragrance: Present during the whole life of the flower.
Persistence: The petals hang on and dry.

Lasting quality: As a cut flower — At least ten days in vase keeping.

REPRODUCTIVE ORGANS

Stamens:
*Number.*—7 To 15.
*Arrangement.*—Encircling the pistils.
*Anthers.*—Size: Less than 4 mm. Color: Whitish.
*Filaments.*—Color — Whitish.
Pistils:
*Number.*—2 Or 3.
*Styles.*—Color — White.
*Stigmas.*—Stigmas have papillas and crests. Color: White.
Characteristics of ovaries: The ovaries are light green in general color and brown at extremity. The ovary surface is clearly ribbed.

The general characteristics of our new carnation cultivar are much like those of "Barstuc" (unpatented), our new flower showing a rounder petal and a purer white color.

We claim:

1. A new and distinct carnation variety, substantially as herein shown and described, characterized by the substantially pure white, medium sized blooms which are produced abundantly during each of its recurrent blooming seasons.

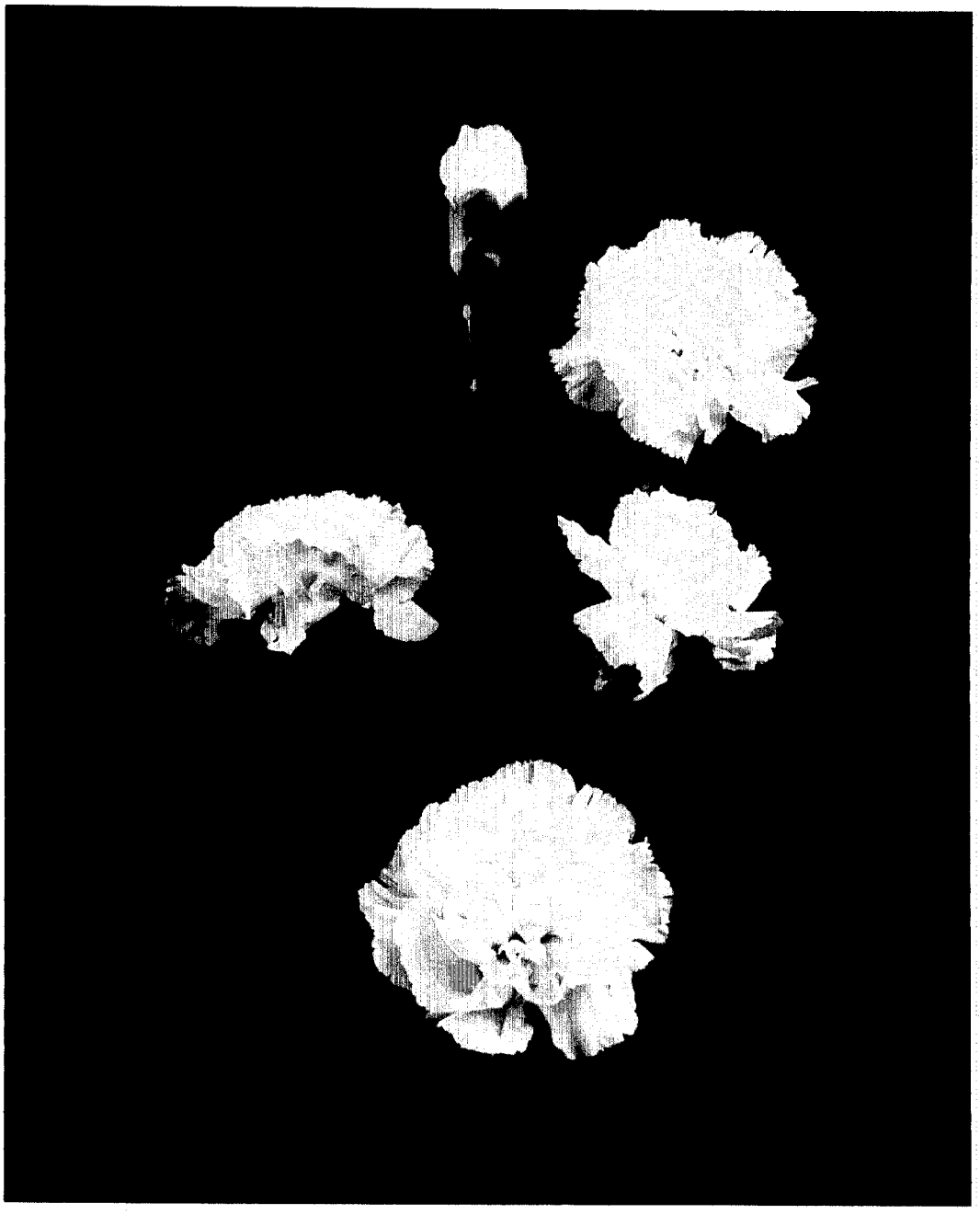

* * * * *